(12) United States Patent
Schwarz et al.

(10) Patent No.: US 8,867,043 B2
(45) Date of Patent: Oct. 21, 2014

(54) METHOD AND DEVICE FOR DETERMINING PROPERTIES OF TEXTURED SURFACES

(75) Inventors: Peter Schwarz, Koenigsdorf (DE); Uwe Sperling, Geretsried (DE)

(73) Assignee: BYK-Gardner GmbH (DE)

( * ) Notice: Subject to any disclaimer, the term of this patent is extended or adjusted under 35 U.S.C. 154(b) by 463 days.

(21) Appl. No.: 12/834,689

(22) Filed: Jul. 12, 2010

(65) Prior Publication Data

US 2011/0013176 A1 Jan. 20, 2011

(30) Foreign Application Priority Data

Jul. 15, 2009 (DE) .......................... 10 2009 033 098

(51) Int. Cl.
| | | |
|---|---|---|
| G01B 11/30 | (2006.01) | |
| G01B 11/06 | (2006.01) | |
| G01N 21/55 | (2014.01) | |

(52) U.S. Cl.
CPC ............ G01B 11/0608 (2013.01); *G01N 21/55* (2013.01)
USPC ............................. 356/600; 356/406; 356/601

(58) Field of Classification Search
CPC . G01N 21/00; G01N 21/27; G01N 2223/606; G01B 11/24; G01J 3/46
USPC ........... 356/600–613, 237.1–239.8, 445–448, 356/236, 237.1–237.5
See application file for complete search history.

(56) References Cited

U.S. PATENT DOCUMENTS

| | | | | |
|---|---|---|---|---|
| 5,155,558 | A * | 10/1992 | Tannenbaum et al. | 356/446 |
| 6,509,964 | B2 * | 1/2003 | Wiles et al. | 356/237.2 |
| 6,538,726 | B2 * | 3/2003 | DeJung et al. | 356/73 |
| 6,542,248 | B1 * | 4/2003 | Schwarz | 356/600 |
| 7,391,518 | B1 * | 6/2008 | Schwarz et al. | 356/446 |
| 7,433,055 | B2 * | 10/2008 | Schwarz et al. | 356/600 |
| 2001/0030744 | A1 * | 10/2001 | Chang | 356/237.3 |
| 2002/0003620 | A1 * | 1/2002 | Jung et al. | 356/73 |
| 2002/0176093 | A1 * | 11/2002 | De Haas et al. | 356/600 |
| 2005/0027482 | A1 * | 2/2005 | Benaoudia et al. | 702/183 |
| 2005/0128484 | A1 * | 6/2005 | Rodrigues et al. | 356/402 |
| 2006/0092417 | A1 * | 5/2006 | Schwarz et al. | 356/337 |
| 2007/0206195 | A1 * | 9/2007 | Sperling | 356/446 |
| 2008/0158239 | A1 * | 7/2008 | Lamy et al. | 345/581 |

FOREIGN PATENT DOCUMENTS

| | | | | |
|---|---|---|---|---|
| DE | 19930688 | * | 1/2001 | ............ G01B 11/30 |
| JP | H11-94767 | | 4/1999 | |
| JP | 2001-041888 | | 2/2001 | |
| JP | 2003-28805 | | 1/2003 | |
| JP | 2008-268190 | | 11/2008 | |
| WO | WO 2008/083206 | | 7/2008 | ............ G06T 15/50 |

OTHER PUBLICATIONS

Chinese Office Action Translation, dated Nov. 1, 2013 (13 pgs).
Japanese Notification of Reason for Rejection, dated Dec. 17, 2013 (12 pgs).

* cited by examiner

*Primary Examiner* — Tarifur Chowdhury
*Assistant Examiner* — Michael P Lapage
(74) *Attorney, Agent, or Firm* — Hayes Soloway P.C.

(57) ABSTRACT

A method of determining optical properties of textured surfaces by irradiation of the surface to be investigated. At least part of the radiation irradiated onto the surface and reflected by the latter is detected by a detector device which permits a location-resolved evaluation of the radiation striking it. A first characteristic value from the radiation detected, characteristic of a texture of the surface is detected. A second characteristic value from the radiation detected, characteristic of a further optical property of the surface is detected. And, a result value is determined on the basis of the first characteristic value and the second characteristic value.

29 Claims, 1 Drawing Sheet

METHOD AND DEVICE FOR DETERMINING PROPERTIES OF TEXTURED SURFACES

BACKGROUND OF THE INVENTION

The present invention relates to a method and a device for determining properties, and in particular optical properties, of textured surfaces. Methods and devices of this type have been known from the prior art for a long time. The invention is described with reference to the surfaces of bodyworks, in particular for vehicles, but it is pointed out that the device according to the invention can also be used in the case of other applications, such as for example in the case of floor coverings, in the case of pieces of furniture, and the like. The textured surface is thus characterized by a topography which as well as a lateral extension also has a vertical profile. The human eye, however, cannot evaluate such differences in height in the micrometer range quantitatively but only observes the effects of this texture. However, the invention is not restricted to the investigation of textured surfaces.

Methods and devices of this type which are known from the prior art usually determine specified properties of the surface, such as for example a colour. In this case these devices are used to derive an objective image of the respective surface. Instruments according to the invention are used in particular in the field of quality assurance, in particular if differences have to be ascertained between two surfaces to be compared. In this case too, however, it is not so much the difference existing in terms of quantity which is crucial but rather the human perception.

A method of simulating surface images is known from WO 2008/083206 A3. In this case a data memory is provided which contains a multiplicity of surface colours and a multiplicity of surface textures. In addition, a processor is present which produces an image of a surface in which case it falls back upon a multiplicity of data stored in the data memory.

In many cases, however, it is less relevant to the user to obtain a precise quantitative analysis of a specific surface. It is more relevant in many cases to establish whether for example a substitute lacquer applied to damaged areas corresponds to the lacquer originally applied, in such a way that is not visible to a customer with the naked eye.

The object of the present invention is therefore to make available a method and a device which in particular also permit such a qualitative evaluation of a surface. In addition, a method should be made available which delivers a rapid overview of qualitative properties of these surfaces in as simple a manner as possible.

SUMMARY OF THE INVENTION

In a method according to the invention for determining properties of in particular textured surfaces, a radiation is first irradiated onto the surface to be investigated. In a further method step at least part of the radiation irradiated onto the surface and reflected by the latter is detected by means of a detector device which permits a location-resolved evaluation of the radiation striking it. In a further method step a first characteristic value is determined from the radiation detected, this first characteristic value being characteristic of a texture of the surface. In a further step a second characteristic value is determined from the radiation detected, the second characteristic value being characteristic of a further optical property of the surface. Finally, a result value is determined on the basis of the first characteristic value and the second characteristic value.

The reflected radiation is radiation which is transmitted from the surface again, for example by way of reflection or by way of diffusion or possibly even diffraction. A characteristic value can also be a difference value.

In this case the detector device not only registers the intensity of the light striking it but permits a location-resolved representation, for example an image display. In this way, for example, this detector device can be a CCD chip or a colour camera.

The first characteristic value can be both a plurality of individual values and an integrated value which emits an intensity distribution from a multiplicity of individual values for example. In this case, however, this first characteristic value, which is characteristic of the texture of the surface, is determined in an optical manner.

In this way the texture of the surface is detected, in particular, without contact.

The second, optical property of the surface is preferably a property which is not correlated with a specified texture of the surface, such as for example a colour property.

On account of a result value being determined on the basis of the two characteristic values, an integral value is obtained which is made up from a number of components. It is preferable for this to be a scalar magnitude. As mentioned in the introduction, it is frequently worthwhile to obtain only qualitative information about the surface, for example information as to whether it can be differentiated optically from a reference surface by the human eye. This information, however, depends upon a multiplicity of criteria of the surface. It is therefore proposed according to the invention that a multiplicity of characteristic values of this type should be combined in a suitable manner in such a way that a qualitative statement on the surface is given and, in particular, a statement as to whether the surface deviates from a reference face in a visually perceptible manner. In this way, a reduction in the information obtained by the measurements per se is carried out intentionally.

It is preferable for a parameter, which is characteristic of the surface and which advantageously correlates with the perception of the human eye, to be determined whilst using the first characteristic value and whilst using at least one further property—known beforehand or determined—of the surface. In this way an adaptation to subjective behaviour of an observer is possible. Even the real observer usually "interprets" visual impressions by adding his or her experiences.

In the prior art structural properties of the surfaces are usually measured in a mechanical manner, for example by a Hommel measuring instrument or the like. Within the scope of the present invention the structural properties are also determined, in particular, in a visual manner. In this case a suitable camera records an image of the textured surface. Considered in itself, however, this image can have a multiplicity of physical causes, for example the presence of actual textures or also the presence of light/dark patterns on the surface. With the method according to the invention it is possible for the physical reason for a recorded image to be better determined on the basis of the previously known or even additionally determined information, such as for example information which can be concluded from the presence of light/dark patterns.

It is advantageous for the result value to be determined on the basis of a multiplicity of stored data which describe optical properties of the surface. These may be both data which describe optical properties of the surface just measured and data which describe reference surfaces.

In a further preferred method at least one further characteristic value, which is characteristic of optical properties of a surface, is used to determine the result value. In this case, therefore, with this method at least three different characteristic values are used to deliver the result value. It is advantageous for at least one characteristic value to be selected from a group of characteristic values which includes a colour of the surface, a brightness of the surface, a DOI (distinctiveness of image) of the surface, a shininess of the surface, a texture of the surface and the like.

It is preferable for at least one characteristic value to be a relative value formed by a comparison. This characteristic value is preferably compared in this case with a reference value and for example a difference or a relationship is formed from these values.

In a further advantageous method the second characteristic value is formed on the basis of a multiplicity of components, at least one of these components being characteristic of the brightness of the surface. It is particularly preferred for at least one of the components to be characteristic of a colour of the surface. In this way, for example, a so-called L-a-b value can be determined, the value L being characteristic of the brightness of the surface, the value a representing a red/green value and the value b representing a yellow/blue value. An unambiguous but qualitative characterization of the surface in question can be obtained by this standardized method. It is also possible, however, for the spectrum to be used to characterize a colour.

The illumination can be both diffuse and directed radiation, in which case these two types of radiation can also be combined during a measurement process. In addition, it is also possible for multilateral illumination to be carried out, for example from annular-segmental light sources. Furthermore, it would be possible to use convergent or divergent radiation or optionally to use a so-called Ulbricht sphere.

It is also possible for filter elements and/or diaphragm elements to be used in the individual radiation paths between the illumination devices and the surface or between the surface and the detector device. These filter elements are used in particular to simulate a specified spectral behaviour of the measuring device in order to correspond as far as possible to a given type of standard light or to obtain a $V_\lambda$ adaptation.

In a further advantageous method individual characteristic values are weighted. In this way it is possible depending upon the surface being investigated, for individual components to be taken into consideration to a greater or lesser degree. This is based on the fact that depending upon the nature of the surface different properties are easier for the human eye to observe than others. In this way, it is known for example that the human eye is more sensitive in certain colour ranges than in others, and it is therefore also easier to perceive colour differences in specific colour ranges than in other ranges.

It is advantageous for a first characteristic value first to be formed for the colour of the surface and for this characteristic value then to be linked to a further characteristic value, such as for example a characteristic value for the texture of the surface. It is preferable to regard said characteristic values as scalar magnitudes. In this way it is possible for the differences mentioned above to be squared.

The invention additionally relates to a device for determining optical properties of surfaces, in which a first radiation device is provided which directs radiation onto a surface to be investigated, and a detector device which detects radiation directed onto the surface from the radiation device and reflected from the surface, the detector device permitting a location-resolved evaluation of the radiation striking the surface. In addition, on the basis of the radiation detected, the detector device delivers at least one first characteristic value which is characteristic of the texture of the surface and one second characteristic value which is characteristic of a further optical property of the surface.

According to the invention the device has a processor device which determines a result value characteristic of the surface on the basis of the first characteristic value and of the second characteristic value. It is therefore proposed with respect to the device that the detector device or a corresponding processor unit should first emit or prepare two separate characteristic values and that these two characteristic values should then be combined by a processor device to form a result value. This result value is preferably also a qualitative or relative value.

In a further advantageous embodiment the device has a memory device in which reference values are stored which act as comparison values for at least the first characteristic value or the second characteristic value. In this way, a specific measurement result is balanced with a stored reference value. For this purpose it is preferable for a comparator to be provided, which compares the values measured in each case with the measured reference values. In this case it is possible for only the result values to be compared with one another, but it is preferable for the individual characteristic values or the components thereof to be compared with one another and for corresponding relative magnitudes, such as for example differences, to be formed.

Instead of a comparison with a reference, however, it would also be possible for the device to measure at different areas, for example of a body, and to compare the measurement results for different areas of this surface. In this way, for example, a measurement could be carried out on a first area of a body, in which case this first area is undamaged, and then a further area on which a replacement lacquer is provided, for example on a replaced door of the vehicle. The values recorded first are then used as reference values.

In a further advantageous embodiment the radiation device irradiates non-directed or diffuse radiation onto the surface to be investigated. It would also be possible, however, for the radiation device to irradiate directed radiation onto the surface so as to simulate for example the illumination with sunlight under a cloudless sky in this way.

In a further advantageous embodiment the device has a memory device in which characteristic values are stored for properties of the surface which are already known. They may be, for example, values characteristic of colours, of shininess, of DOI and the like.

In a further advantageous embodiment the device has a distance-measuring device in order to determine paths covered by the device with respect to the surface. In this way a qualitative image of relatively large surfaces can be determined and, in particular, a geometrical correlation with specified points on the surface can be carried out. The distance-measuring device can be for example a rangefinder arranged on a wheel, the device being moved over the surface with the aid of this wheel.

It is also possible, however, for distances to be established in that a precise geometrical position of the device with respect to an environment is detected and a corresponding distance is triangulated on the basis of a plurality of these values. In this way for example, the device could be arranged on a robot arm, the position of which is determined with reference to robot co-ordinates for example.

In a further advantageous embodiment the radiation device and the detection device are provided inside a housing, this housing having only one opening for the investigating surface and being otherwise closed. As mentioned, the device advantageously has a wheel in order to move this device with respect to the surface. It is advantageous for a plurality of wheels to be provided so that at the same time a defined position of the device with respect to the surface may be observed.

In a further advantageous embodiment the device has a plurality of radiation devices which irradiate the surface at a plurality of different angles for example. It would also be possible for a plurality of detection devices to be provided which record the radiation reflected by the surface. It is advantageous for the radiation devices to irradiate white light or standardized light, such as for example D65 light onto the surface to be investigated. In addition, in an advantageous embodiment a diaphragm is arranged between the surface and the detection device. This diaphragm can be both a mechanical diaphragm and a software diaphragm. In the latter case the "diaphragm" can be set by a suitable change in the image portion observed or in a defined pixel field. In this case the image-recording device can be understood as being a programmed pixel field (CCD or CMOS) camera.

It is therefore preferably possible for the image recorded by the image-recording device or the recorded image extract thereof to be changed. As a result of this change in the resolution or as a result of the change in the image extract, information can be obtained on textures of the surface. Measures such as a sliding average formation can also be taken for this purpose.

For example, a radiation device is arranged at an angle of 45° with respect to the surface. The radiation-detector device is advantageously provided at 0° with respect to the surface. In this case it is possible for a plurality of radiation devices to be activated simultaneously, but a successive activation would also be possible.

In a further advantageous embodiment the radiation directions extending between the radiation devices and the radiation-detector devices are situated in one plane. This is relevant in particular when a plurality of radiation devices or a plurality of radiation-detector devices are provided. In this case all the geometrical radiation directions are advantageously situated in a pre-determined plane. It is also possible for undesired shadow effects to be prevented by suitable illumination, in particular from a multiplicity of directions.

BRIEF DESCRIPTION OF THE DRAWINGS

Further advantages of the present invention may be seen in the accompanying drawings, in which.

DETAILED DESCRIPTION OF THE INVENTION

Figure 1:
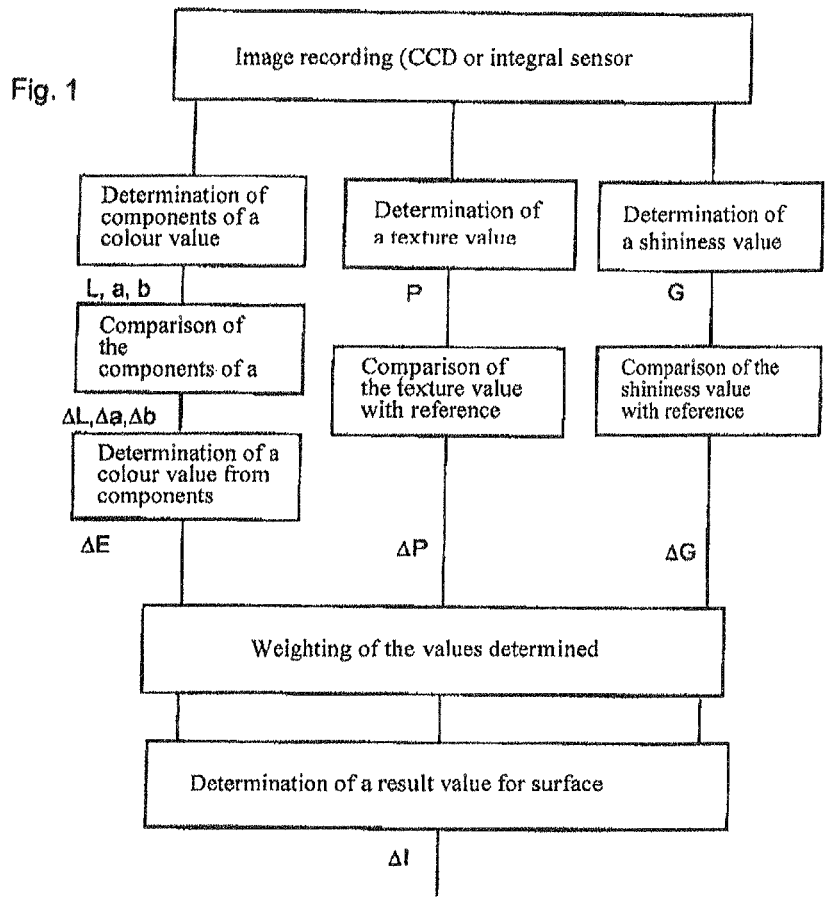
FIG. 1 is a flow chart for a method according to the invention.

FIG. 1 is a diagrammatic illustration of the sequence of a method according to the invention. In this case an image of a surface to be investigated is first recorded with the device according to the invention. The surface can be irradiated for example by means of a radiation device and the light thrown back from the surface, i.e. in particular reflected or diffused light, can be recorded by the image-recording device.

The components L-a-b of a colour value on the one hand and a texture value P and also a shininess value G of the surface on the other hand are determined from the data obtained by means of the image recording. In this case the texture value P can first be determined in that, starting from the recorded image, a statistical value is formed (for example a variance, an entropy, fractal elements, a grey-scale matrix, a grey-scale histogram and parameters thereof such as centre of gravity, half-width or other threshold values or other mathematical methods of evaluating one- or two-dimensional images), which for example takes into consideration the differences in intensity of various pixels.

The shininess value G can be determined for example in that two different radiation devices are irradiated onto the surface at different angles and the image-recording device, in front of which a diaphragm is preferably arranged, records the respective images and determines corresponding intensity values, in this case therefore advantageously determines intensity only striking the image-recording device. In this way a spatial intensity distribution or the integral of the intensity reflected by the surface is determined in order to determine the shininess value.

It would also be possible to determine other optical characteristic values with the aid of diaphragms or, on the other hand, to make the radiation device and/or the detector device movable in the peripheral direction, so that radiation can be irradiated at different angles with the same radiation device and/or radiation can be detected at different angles with the detector device 4. In addition, a plurality of radiation sources can also be activated simultaneously or in succession.

In this case the optical device used images onto the camera the surface to be investigated, but it is also possible for the illumination diaphragm mirrored by way of the surface to be imaged onto the camera.

The colour values L-a-b are determined by the use of a colour camera or an integral sensor such as a photocell. The individual colour values L-a-b are compared with a reference below, so that corresponding difference values $\Delta L$, $\Delta a$ and $\Delta a$ result. A colour difference $\Delta E$ is determined from these difference values in accordance with the following equation:

$$\Delta E = \sqrt{\Delta L^2 + \Delta a^2 + \Delta b^2}$$

In this way the colour difference $\Delta E$ describes the deviation of the determined colour values from a reference pattern or a reference colour.

In a similar manner the texture value determined is compared with a reference value and a value P or a difference value $\Delta P$ is determined. The same is also carried out for the shininess value G which is compared with a reference value and a value $\Delta G$ is determined in this way. In this case it is possible for all the values to be determined with the same detector device, in particular if this detector device is a colour camera. A camera arrangement is also possible however, which has a plurality of filters capable of being positioned in front in succession (optionally also a filter wheel).

In a further step a weighting of the individual values (not shown) can be carried out, which can also depend inter alia upon the surface used. Finally, a result for $\Delta I$ is determined for the surface in accordance with the following equation:

$$\Delta I = \sqrt{e\Delta E^2 + f\Delta P^2 + g\Delta G^2}.$$

In this way, in order to determine the result value $\Delta I$, the deviations of the individual components $\Delta E$, $\Delta P$ and $\Delta G$ are also determined, and these in turn are combined integratively, optionally whilst using coefficients e, f, g. These coefficients e, f, g can also, however, be variable. The result value $\Delta I$ makes a statement as to whether the optical impression of a surface differs to a perceptible degree from a reference surface for the user.

In the above formulae, however, it is also possible for absolute values to be used instead of the difference values illustrated.

Figure 2:
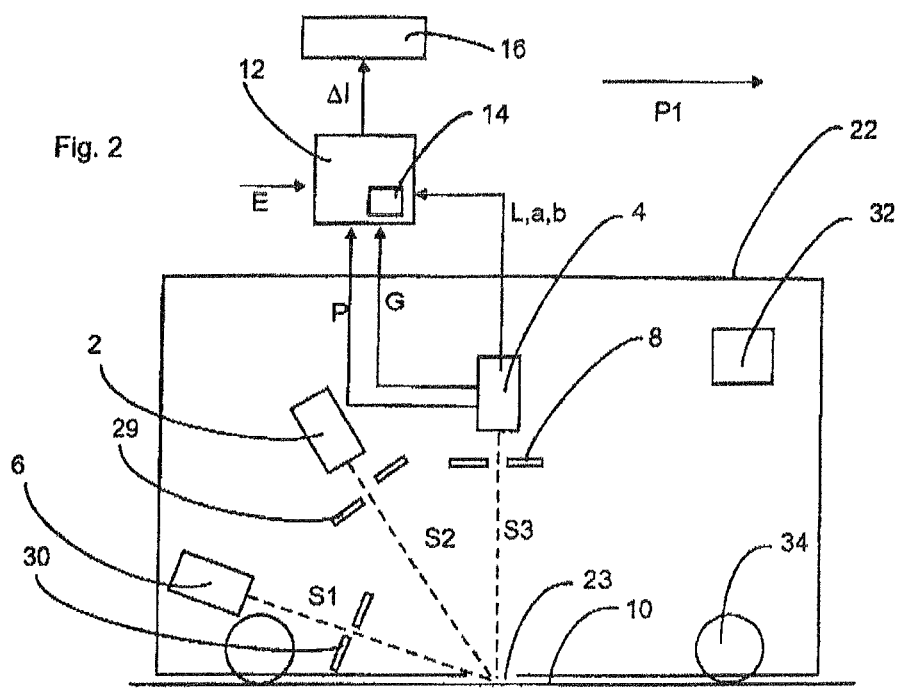
FIG. 2 is an overall diagrammatic illustration of a device according to the invention.

FIG. 2 is an overall diagrammatic illustration of a device according to the invention. This device has a housing 22 which is closed apart from an opening 23, this opening being used for observing a surface 10. The reference numbers 2 and 6 designate two radiation devices which irradiate light onto the surface 10 at different angles. A detector device 4 records the radiation thrown back from the surface, in particular diffused or reflected radiation. In the optical path between the surface and detection device a diaphragm is located. The reference numbers 29 and 30 designate further diaphragms and/or filter devices which are arranged in the respective radiation paths between the radiation devices 2 and 12 and the surface.

The detector or image-recording device delivers the values P, G, L, a, b to a processor device 12 which processes these values. In detail, the result value ΔI which can be shown by means of a display device 16 is determined by the processor device 12 in accordance with the diagram shown in FIG. 1.

The reference number 14 designates a memory device in which reference values, for example colour values, texture values or shininess values are stored. In addition, the processor device 12 can have added to it external values E which are used for processing and, for example, for determining the values ΔP. The latter contain information on the surface observed, so that the processor device can decide whether a specified value results from existing textures or is only the consequence of different intensity distributions or contrasts. This information cannot be obtained directly from the recorded image, but only by using additional data, which in particular describe the surface under investigation or which are obtained by additional measurements with the different measurement geometries.

The reference number 32 designates a control device to actuate for example the radiation devices 2 and 6 and optionally also the detector device. In this way, in the framework of a specific measurement module, it would be possible for example for the surface to be illuminated in succession by the two radiation devices 2 and 6 and then for the two images to be evaluated by the processor device 12. The reference signs S1, S2 and S3 designate radiation directions of the radiation irradiated onto the surface 10 or reflected by the latter. It is advantageous for the two radiation directions S1 and S2 and the radiation direction S3, which extends from the surface 10 in the direction of the image-recording device 4, to be situated in one plane. It would also be possible, however, for detectors or radiation sources for example to be arranged outside the measurement plane.

The reference number 34 designates a rolling device or a wheel which allows the device 1 to move with respect to the surface in accordance with the arrow P1. In addition, the device 1 has a distance-measuring device (not shown) which determines paths which are covered by the device with respect to the surface 10. In this way, the surface can be measured with geometrical correlation in each case. A distance-measuring device of this kind could be coupled to the wheels 34. It would also be possible, however, for the device 1 to be arranged on a stand, for example a robot arm, and in this way to be moved in a defined manner with respect to the surface 10.

In this case, in contrast to FIG. 1, the individual processor devices and memory devices 12 and 14 are not arranged outside the housing 22 but preferably inside the housing or in a portion of an electronic device provided for this purpose. The diaphragms mentioned can be used to determine shine effects of the surface. It would also be possible, however, for the diaphragms to be formed by the image evaluation, i.e. in the form of "software diaphragms", for example in that only specified areas of an image are evaluated.

All the features disclosed in the application documents are claimed as being essential to the invention, insofar as they are novel either individually or in combination as compared with the prior art.

LIST OF REFERENCES 1 device
2 radiation device
4 detector device
6 further radiation device
8 diaphragm
10 surface
12 processor device
14 memory device
16 display device
22 housing
23 opening
29, 30 diaphragms
34 wheel
ΔP first characteristic value
ΔE second characteristic value
ΔG characteristic value
ΔI result value
G, E, P parameter
L, a, b colour values
E property
P1 direction of movement
S1, S2, S3 radiation directions

The invention claimed is:

1. A method of determining properties of in particular textured surfaces comprising the steps of:
    irradiation of radiation onto the surface to be investigated;
    detection of at least part of the radiation irradiated onto the surface and reflected by the latter by means of a detector device, selected from the group consisting of a CCD chip, a colour camera, a CMOS camera and an integral sensor which permits a location-resolved evaluation of the radiation striking it, wherein the irradiation and the detection takes place within a housing which is closed apart from an opening used for observing the surface;
    determination of a first characteristic value (P) from the radiation detected, wherein the first characteristic value (P) is an integrated value which corresponds to an intensity distribution from a multiplicity of individual values, and wherein the first characteristic value (P) is characteristic of a texture of the surface;
    determination of a second characteristic value (ΔE) from the radiation detected, wherein the second characteristic value is characteristic of a further optical property of the surface, which is not correlated with a specific texture of the surface;
    determination of a result value (ΔI) on the basis of the first characteristic value (P) and the second characteristic value (ΔE).

2. A method according to claim 1, wherein a parameter which is characteristic of the surface is determined whilst using the first characteristic value (P) and whilst using at least one further property—known beforehand or determined—of the surface.

3. A method according to claim 2, wherein a parameter which is characteristic of the surface is determined whilst using the first characteristic value (P) and whilst using at least one further property—known beforehand or determined—of the surface.

4. A method according to claim 2, wherein the result value ($\Delta I$) is determined on the basis of a multiplicity of stored data which describe optical properties of the surface.

5. A method according to claim 2, wherein at least one further characteristic value ($\Delta G$), which is characteristic of optical properties of the surface, is used to determine the result value ($\Delta I$).

6. A method according to claim 2, wherein at least one characteristic value is selected from a group of characteristic values which includes a colour of the surface, a brightness of the surface, a shininess of the surface, and a texture of the surface.

7. A method according to claim 2, wherein at least one characteristic value (P, $\Delta E$) is a relative value formed by a comparison.

8. A method according to claim 2, wherein the second characteristic value ($\Delta E$) is formed on the basis of a multiplicity of components ($\Delta L$, $\Delta a$, $\Delta b$), wherein at least one of these components ($\Delta L$) is characteristic of the brightness of the surface.

9. A method according to claim 8, wherein at least one of the components ($\Delta L$, $\Delta a$, $\Delta b$) is characteristic of a colour of the surface.

10. A method according to claim 1, wherein the result value ($\Delta I$) is determined on the basis of a multiplicity of stored data which describe optical properties of the surface.

11. A method according to claim 10, wherein at least one characteristic value is a relative value formed by a comparison.

12. A method according to claim 1, wherein at least one further characteristic value ($\Delta G$), which is characteristic of optical properties of the surface, is used to determine the result value ($\Delta I$).

13. A method according to claim 1, wherein at least one characteristic value is selected from a group of characteristic values which includes a colour of the surface, a brightness of the surface, a shininess of the surface, and a texture of the surface.

14. A method according to claim 1, wherein at least one characteristic value (P, $\Delta E$) is a relative value formed by a comparison.

15. A method according to claim 14, wherein the characteristic value is compared with a reference value.

16. A method according to claim 1, wherein the second characteristic value ($\Delta E$) is formed on the basis of a multiplicity of components ($\Delta L$, $\Delta a$, $\Delta b$), wherein at least one of these components ($\Delta L$) being characteristic of the brightness of the surface.

17. A method according to claim 16, wherein at least one of the components ($\Delta L$, $\Delta a$, $\Delta b$) to be characteristic of a colour of the surface.

18. A method according to claim 16, wherein a second component (a) represents a red/green value and a third component (b) represents a yellow/blue component and the three components form a L-a-b value.

19. A method according to claim 18, wherein colour values L-a-b are determined by the use of a colour camera or an integral sensor.

20. A method according to claim 1, wherein the individual characteristic values are weighted.

21. A method according to claim 20, wherein $\Delta I$ is determined for the surface with the following equation $\Delta I = \sqrt{e\Delta E^2 + f P^2 + g \Delta G^2}$, wherein e, f and g are weighting factors and $\Delta G$ is either 0 or another optional characteristic value.

22. A method according to claim 1, wherein the characteristic values are scalar magnitudes.

23. A device for determining optical properties of surfaces, comprising inside a housing, which is closed apart from an opening used for observing the surface, a first light source for directing light radiation onto a surface to be investigated, and a detector device, selected from the group consisting of a CCD chip, a colour camera, a CMOS camera and an integral sensor, for detecting light radiation reflected from the surface, wherein the detector device permits a location-resolved evaluation of the light radiation detected and delivers at least one first characteristic value ($\Delta P$) which is an integrated value which corresponds to an intensity distribution from a multiplicity of individual values, and which is characteristic of a texture and one second characteristic value ($\Delta E$) which is characteristic of a further optical property of the surface, which is not correlated with a specific texture of the surface wherein the device has a processor device and a memory device which receives a signal from the light detector and processes the signal to determine a result value ($\Delta I$) characteristic of the surface on the basis of the first characteristic value ($\Delta P$) and of the second characteristic value ($\Delta E$).

24. A device according to claim 23, wherein the device has a memory device in which reference values are stored which act as comparison values for determining at least the first characteristic value ($\Delta P$) or the second characteristic value ($\Delta E$).

25. A device according to claim 23, wherein the memory device in which characteristic values are stored contains properties of the surface which are already known.

26. A device according to claim 23, wherein the device has a plurality of light sources which irradiate the surface at a plurality of different angles.

27. A device according to claim 23, wherein the device has a plurality of light detection devices which record the radiation reflected by the surface.

28. A device according to claim 23, wherein the light detector device records the reflected radiation thrown back from the surface.

29. A device according to claim 23, wherein $\Delta I$ is determined for the surface with the following equation $\Delta I = \sqrt{e\Delta E^2 + f P^2 + g \Delta G^2}$, wherein e, f and g are weighting factors and $\Delta G$ is either 0 or another optional characteristic value.

* * * * *